(12) United States Patent
Noblett

(10) Patent No.: US 6,471,916 B1
(45) Date of Patent: Oct. 29, 2002

(54) APPARATUS AND METHOD FOR CALIBRATION OF A MICROARRAY SCANNING SYSTEM

(75) Inventor: David Noblett, Oak Park, CA (US)

(73) Assignee: Packard Instrument Company, Meriden, CT (US)

( * ) Notice: Subject to any disclaimer, the term of this patent is extended or adjusted under 35 U.S.C. 154(b) by 0 days.

(21) Appl. No.: 09/437,039

(22) Filed: Nov. 9, 1999

(51) Int. Cl.⁷ .............................................. G01N 21/64
(52) U.S. Cl. ................................ 422/82.08; 422/82.05; 436/8; 436/164; 436/172; 435/808; 250/252.1; 250/458.1; 356/317
(58) Field of Search ....................... 422/82.05, 82.08; 436/8, 63, 164, 165, 172; 435/808; 250/458.1, 459.1, 252.1; 356/317

(56) References Cited

U.S. PATENT DOCUMENTS

| | | | | |
|---|---|---|---|---|
| 3,973,129 A | * | 8/1976 | Blumberg et al. | 250/461.2 |
| 3,988,591 A | * | 10/1976 | Killer | 250/565 |
| 5,091,652 A | * | 2/1992 | Mathies et al. | 250/458.1 |
| 5,585,639 A | * | 12/1996 | Dorsel et al. | 250/458.1 |
| 5,689,110 A | | 11/1997 | Dietz et al. | 250/252.1 |
| 5,742,380 A | * | 4/1998 | Ronn | 356/39 |
| 5,798,206 A | * | 8/1998 | Neurath et al. | 435/5 |
| 5,838,435 A | | 11/1998 | Sandison | 356/243 |
| 6,075,613 A | * | 6/2000 | Schermer et al. | 356/446 |
| 6,078,390 A | * | 6/2000 | Bengtsson | 356/318 |
| 6,215,894 B1 | * | 4/2001 | Zeleny et al. | 382/133 |
| 6,245,517 B1 | * | 6/2001 | Chen et al. | 435/6 |
| 6,251,601 B1 | * | 6/2001 | Bao et al. | 435/6 |

FOREIGN PATENT DOCUMENTS

EP 0440342 A2 8/1991

* cited by examiner

Primary Examiner—Maureen M. Wallenhorst
(74) Attorney, Agent, or Firm—Cesari and McKenna, LLP

(57) ABSTRACT

A microarray scanning system for conducting microarray experiments on a planar substrate includes an excitation radiation source, a detection system, and a computational device, the planar substrate supporting a plurality of dilution marks containing a fluorophore and located on the substrate surface at predetermined distances from a fiduciual reference mark and/or a microarray. Automatic calibration adjustment of either or both the detection system and the excitation radiation source is achieved via the computational device by irradiating the dilution spots, detecting emission radiation produced by the dilution spot fluorophore material, deriving a series of brightness readings from the levels of emission radiation detected at corresponding dilution spots; analyzing the brightness readings to obtain a fluorophore brightness characteristic as a function of concentration; and adjusting the sensitivity of the detection system and/or the intensity level of the source of excitation radiation in accordance with the fluorophore brightness characteristic.

13 Claims, 4 Drawing Sheets

APPARATUS AND METHOD FOR CALIBRATION OF A MICROARRAY SCANNING SYSTEM

CROSS REFERENCE TO RELATED APPLICATION

This application is related to co-pending, commonly-assigned Application entitled "Apparatus and Method for Using Fiducial Marks on a Microarray Substrate," which was filed on Nov. 9, 1999 as application Ser. No. 09/436,974 and issued as U.S. Pat. No. 6,362,004 on Mar. 26, 2002.

BACKGROUND OF THE INVENTION

1. Field of the Invention

This invention in general relates to optical scanning systems and, in particular, to an apparatus and method for calibration of a microarray scanning system.

2. Description of the Prior Art

The use of excitation radiation to produce fluorescence in a series of scanned genetic samples is known. U.S. Pat. No. 5,689,110 issued to Dietz et al., for example, discloses a calibration method and device for a fluorescence spectrometer which uses fluorescence from a homogenous solid state standard as the source of calibration fluorescence. Fluorescent imagers are used to acquire data in experiments that utilize fluorescent labels, or fluorophores, to identify the state of a sample being tested. In some cases the presence of or lack of fluorophores in the sample determines the experimental result. In other cases the fluorophore concentration, which is a function of the intensity of the emission radiation received from the sample, is the measurement of interest and the experimental result can be inferred by measuring the intensity of the detected radiation.

An example of a process that uses fluorophores is the microarray which is a set of experiments utilizing genetic material such as DNA or RNA, bound to a glass substrate. Reference or 'target' DNA is spotted onto a glass substrate—typically a one-by three-inch glass microscope slide—where it chemically binds to the surface. Each spot, or sample, of DNA constitutes a separate experiment. A sample of 'probe' DNA or RNA, to which has been added the fluorophore material, is subsequently placed on the target spots on the surface of the substrate and is allowed to hybridize with the target DNA. Excess probe DNA that does not bind with target DNA is removed from the surface of the slide in a subsequent washing process.

The experiments measure the binding affinities between the probe DNA and the target DNA to determine the similarity in molecular structure; complementary molecules have a much greater probability of binding than do unrelated molecules. The fluorophore added to the probe DNA emits a range of radiation energy centered about a wavelength $\lambda_{emission}$ when illuminated by incident excitation radiation of a particular, shorter wavelength $\lambda_{exitation}$. The brightness of the emitted radiation, measured by the detection system of a microarray scanning system, is a function of the fluorophore concentration present in the illuminated spot. Because the fluorophore concentration is a function of the binding affinity or likeness of the probe molecule to the target molecule, the brightness of a hybridized spot is an indication of the degree of similarity between the probe DNA and the target DNA present in the hybridized spot. A typical microarray sample may provide for up to tens of thousands of experiments to be performed simultaneously on the probe DNA, thus producing a detailed characterization of a particular gene under investigation.

In a microarray scanning system, the area of interest is usually divided into an array of discrete elements referred to as 'pixels.' Each pixel is illuminated independently as it is being addressed by the scanning system. The optical radiation source is typically a single-wavelength laser device focused down to form an excitation radiation spot of the desired size. Emission radiation is emitted by the illuminated fluorophore in an outward, spherical beam. A portion of this emission beam is collected by an optical system and transmitted to a detection apparatus. In addition to the emitted radiation, some of the incident excitation radiation scattered from the surface of the sample is also collected by the optical system. To minimize the amount of excitation radiation reaching the detector assembly, the optical system may be designed using filtering components, such as dichroic and band-pass filters, to provide discrimination between excitation and emission radiation wavelengths.

In order to obtain accurate information from the scanning of a microarray, it is important to know which fluorophore materials have been used in order to use the correct wavelengths in illuminating the spots and to filter the correct wavelengths of the fluorescent emissions. Furthermore, it is advantageous to excite the fluorophores with a high-intensity excitation beam so as to return the maximum signal to the microarray scanning system detector. However, the intensity of the excitation beam must be kept below the level at which the flurophore becomes saturated or the sample material may degrade.

Furthermore, analysis of raw data collected by the microarray scanning system must be performed in accordance with protocols that may vary in accordance with experiment parameters. In conventional scanning systems, entry of the scanning and analysis protocols is performed manually. This involves significant operator time and, further, is a source of errors in the scanning and analysis procedure.

The sensitivity of the detection system is a critical parameter in a microarray scanning system. The possible range of fluorescence emission varies enormously between samples and often exceeds the dynamic range of the detection system, causing saturation of signals. The occurrence of saturated signals in a data set makes it impossible to quantify the fluorophore brightness emitted from the hybridized spots exhibiting saturation.

In a conventional microarray scanning system, sensitivity adjustment of the detection system is an iterative procedure. The user performs a partial scan using a particular channel of the system, views the image, and adjusts the excitation radiation power and/or the gain of the detector system accordingly such that the optimal range of sensitivity lies within the dynamic range of the detection system. This process is time consuming for the user and, further, degrades the experimental samples by a process of photobleaching the fluorescently-tagged spots on the substrate.

While the relevant art provides iterative procedures for calibration of microarray scanning systems, there remains a need for improvements that offer advantages and capabilities not found in presently available methods of calibration, and it is a primary object of this invention to provide such improvements.

It is another object of the present invention to provide a automatic method of calibrating a microarray scanning system.

It is a further object of the present invention to provide such a calibration method which is performed without damage to the sample microarray.

It is yet another object of the present invention to provide a microarray sample configuration which includes an automatic calibration feature.

Other objects of the invention will be obvious, in part, and, in part, will become apparent when reading the detailed description to follow.

SUMMARY OF THE INVENTION

In accordance with the present invention a series of dilution spots is imprinted on a microarray sample which includes an array of genetic material samples containing one or more fluorophores. A microarray scanning system, which includes an excitation radiation source, a detection system, and a computational device, is used to analyze the fluorophores in the genetic material samples. Automatic calibration adjustment of either or both the detection system and the excitation radiation source is achieved by i) irradiating the dilution spots with the source of excitation radiation; ii) detecting emission radiation produced by the dilution spot fluorophore material in response to the irradiation; iii) deriving a series of brightness readings corresponding to the levels of emission radiation detected at corresponding dilution spots; iv) analyzing the brightness readings with the computational device to obtain a fluorophore brightness characteristic as a function of fluorophore concentration; and v) adjusting the sensitivity of the detection system and/or the intensity level of the source of excitation radiation in accordance with the fluorophore brightness characteristic.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
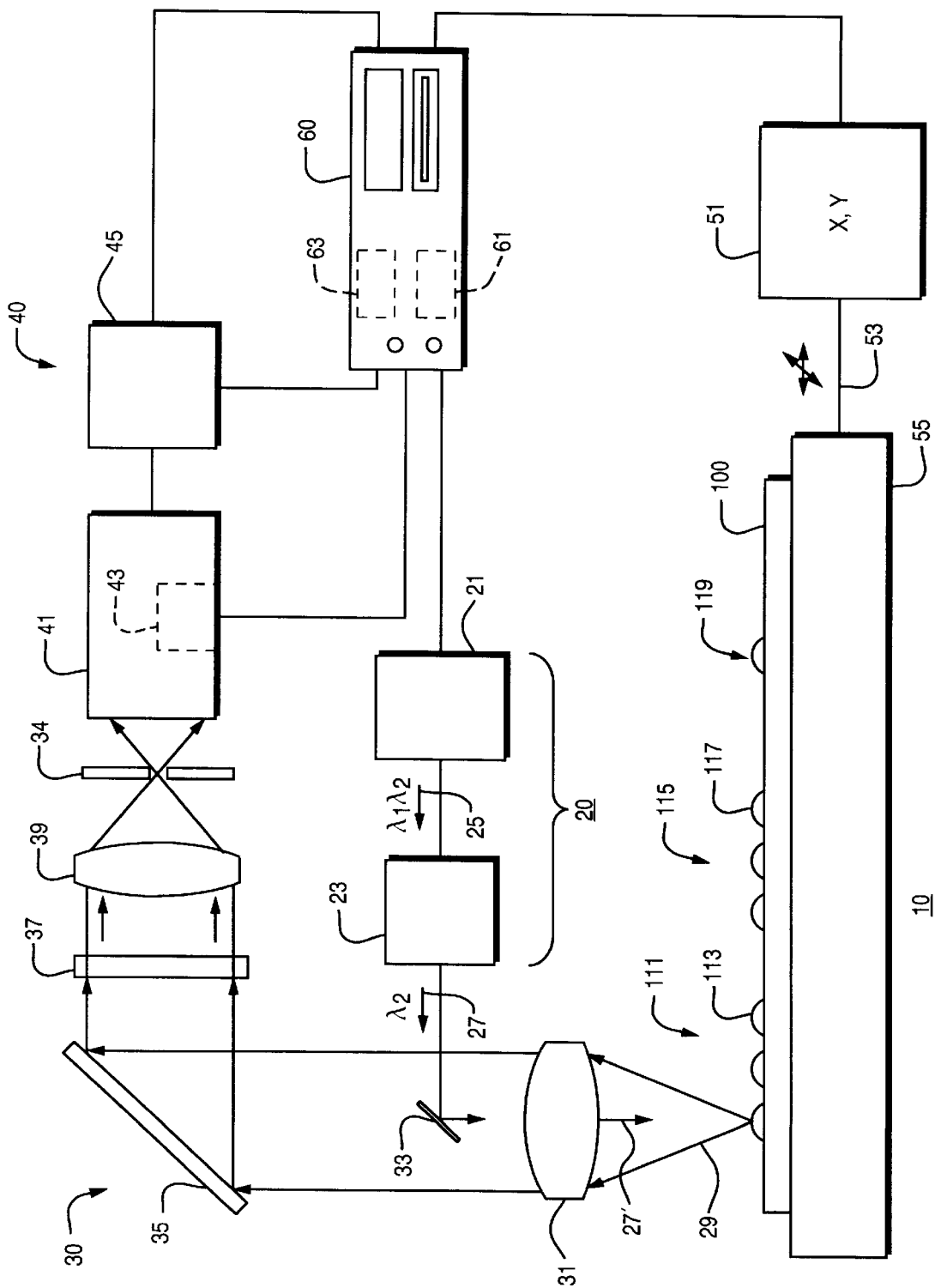
FIG. 1 is a diagrammatical view of a microarray scanning system as used in the analysis of a microarray sample.

There is shown in FIG. 1 a diagrammatical representation of a microarray scanning system 10 as can be used in the analysis of a microarray sample 100. The microarray scanning system 10 includes an illumination head 20, an optical system 30, and a detector assembly 40. The illumination head 20 comprises an excitation radiation source 21 producing source radiation 25 of two or more different wavelengths and a shutter assembly 23 which functions to pass any one of the different wavelengths received from the excitation radiation source 21. In the example shown, the excitation radiation source 21 is producing radiation 25 having wavelength $\lambda_1$ and wavelength $\lambda_2$. The shutter assembly 23 is blocking radiation of wavelength $\lambda_1$ and is allowing radiation of wavelength $\lambda_2$ to pass as a beam of single-wavelength excitation radiation 27. The excitation radiation source 21 may include, for example, two or more single-wavelength coherent optical radiation sources such as lasers, one or more multi-wavelength coherent optical radiation sources, or one or more broadband sources. It should thus be understood that operation of the microarray scanning system 10 is not limited to the use of only two wavelengths and that the illumination head 20 may provide excitation radiation of three or more different wavelengths.

The optical system 30 includes an excitation mirror 33 positioned to redirect the excitation radiation beam 27 onto the microarray sample 100 as an incident excitation beam 27'. An objective lens 31 is disposed between the excitation mirror 33 and the microarray sample 100 in the optical path of the incident excitation radiation beam 27'. The objective lens 31 serves to focus the incident excitation beam 27' to a desired spot size on the microarray sample 100.

When the incident excitation radiation 27' illuminates a fluorescent label, or fluorophore, present in the microarray sample 100, there is produced a corresponding emission radiation beam 29 of wavelength $\lambda_{emission}$, typically 20 to 40 nm longer than the wavelength (i.e., $\lambda_1$ or $\lambda_2$) of the incident radiation beam 27'. In the configuration shown, the excitation mirror 33 functions as a geometric beamsplitter where the width of the incident excitation beam 27' is much smaller than the width of the emission radiation beam 29. The relatively small excitation mirror 33 thus reflects the incident excitation beam 27' scattered from the microarray sample 100 back to the illumination head 20 while allowing the greater portion of the emission radiation beam 29 to pass upstream of the objective lens 31.

The detector assembly 40 includes a photomultiplier tube 41 and a variable high-voltage reference 43. In an alternative embodiment, an avalanche photodiode or a solid state optical detection device (e.g., a CCD) can be used in place of the photomultiplier tube 41. The photomultiplier tube 41 outputs a signal to a variable-gain amplifier 45.

A band-pass or long-pass filter 37, substantially transmissive to the emission radiation beam 29 and substantially non-transmissive to the excitation radiation beam 27 may be disposed in the optical path of the optical system 30 between the objective lens 31 and a focusing lens 39. In a preferred embodiment, the focusing lens 39 forms a confocal system with the objective lens 31 and images the emission radiation beam 29 onto the photomultiplier tube 41. The optical system 30 may further include a broadband mirror 35 to provide a folded transmission path for the emission radiation beam 29, and an aperture stop 34 may be provided between the focusing lens 39 and the photomultiplier tube 41. The aperture stop 34 serves to block that portion of the illuminated microarray sample 100 which is not in focus at the photomultiplier tube 41. As can be appreciated by one skilled in the relevant art, the microarray scanning system 10 may further include a corresponding band-pass or long-pass filter for each of the other excitation-emission wavelength pairs utilized by the microarray scanning system 10.

The operation of the microarray scanning system 10 can best be described with reference to FIG. 1 and to FIG. 2 which is a diagrammatical plan view of the microarray sample 100. The microarray sample 100 includes a planar substrate 101, such as a one-by three-inch glass microscope slide. A sample surface 103 of the planar substrate 101 may, for example, include a marking 105 and/or an etched or 'frosted' region 107 extending from a boundary 108 to the edge of the planar substrate, either or both produced by the substrate manufacturer. The microarray sample 100 includes at least a first microarray 111 comprising a plurality of first target spots 113 (denoted by open circles), containing genetic target material, disposed on the sample surface 103 and may further include a second microarray 115 comprising a plurality of second target spots 117. The first target spots 113 and second target spots 117 are typically arrayed in rows and columns as shown. As probe material (not shown)

containing a predetermined concentration of fluorophore material is added to successive first target spots 113, hybridized spots 114 (denoted by filled circles) remain after excess probe material is removed. Similarly, hybridized spots 118 result from the addition of probe material to second target spots 117.

The microarray sample 100 is removably secured to a test platform 55, in FIG. 1, such as by mechanical restraint or by a suction device, as is well-known in the relevant art. A positioning system 51 imparts translational movement in an X-Y plane to the test platform 55, and thus to the microarray sample 100, by means of a mechanical linkage 53. The microarray scanning system 10 further includes a computational device 60, such as a computer, connected to the positioning system 51 so as to provide control by the computational device 60 via positioning software 61. When the microarray sample 100 has been secured to the test platform 55, the detector assembly 40 can be used to optimize the focus position of the objective lens 31. This can be done, for example, by imaging the marking 105 or a user-applied fiducial mark 106 with the optical system 30. The focusing procedure is described in greater detail in the related application, incorporated herein in its entirety by reference.

The computational device 60 also receives the signal output of the variable-gain amplifier 45, which provides positional feedback as the microarray sample 100 is aligned and scanned via the positioning system 51. The positional feedback obtained by illuminating the test surface 103 with the incident excitation radiation 27' and imaging the illuminated portion of the test surface 103 back to the positioning software 61 via the detector 40 as the microarray sample 100 is moved in the X-Y plane.

Figure 2:
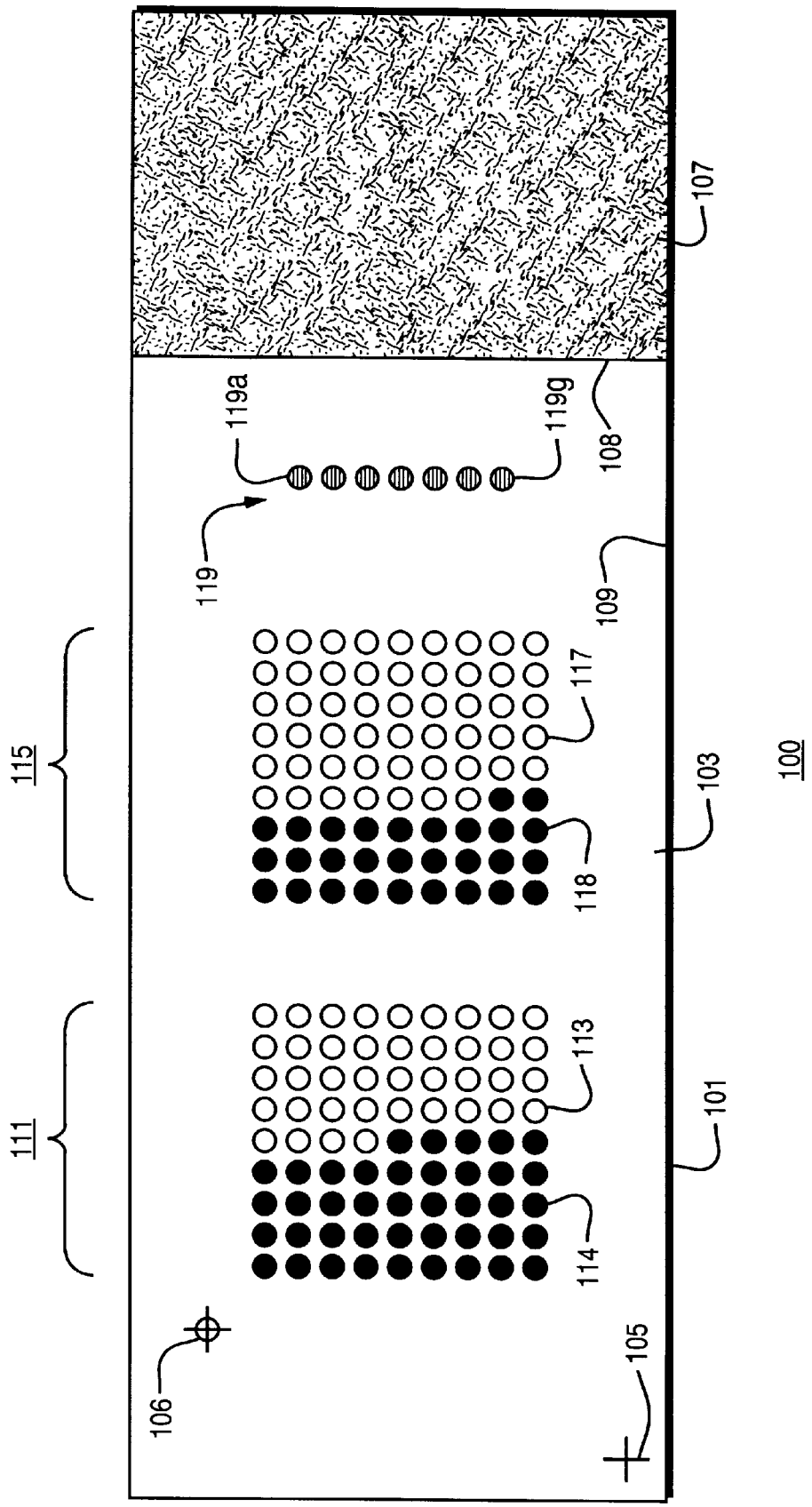
FIG. 2 is a diagrammatical view of the sample surface of the microarray sample of FIG. 1.

The sensitivity of the microarray scanning system can be adjusted for a particular microarray sample 100 by using a dilution spots 119 provided on the sample surface 103, in FIG. 2. The dilution spots 119 includes a plurality of dilution spots 119a through 119g each having a different fluorophore concentration. The user quantifies the dilution spots 119 on a spot-by-spot basis to obtain a concentration-to-brightness curve for a particular fluorophore. It should be understood that although seven dilution spots are shown, a greater or lesser number can be used.

In a preferred embodiment, the first microarray 111, the second microarray 115, and the dilution spots 119 are placed at predetermined positions relative to one another by using as a reference feature any of, for example, the marking 105, the etched region 107 and boundary 108, the user-applied fiducial mark 106, or an edge 109 of the substrate 101. This configuration enables use of automated equipment to image the first microarray 111, the second microarray 115, and the dilution spots 119, and to perform subsequent calibration as described in greater detail below.

The microarray scanning system 10 divides the dilution spots 119 into pixels. As the fluorophore material in each of the dilution spots 119a through 119g is illuminated by the incident excitation radiation 27', each pixel is successively acquired by the detector assembly 40 and analyzed for the presence of fluorophore material by the computational device 60. Each analysis measurement results in a data point that represents the relative fluorophore concentration of the measured pixel. The pixel data is then reconstructed to produce a quantified description of the scanned dilution spots 119. A similar procedure is used to analyze the fluorescent emission from the hybridized spots 114 and 118.

Figure 3:
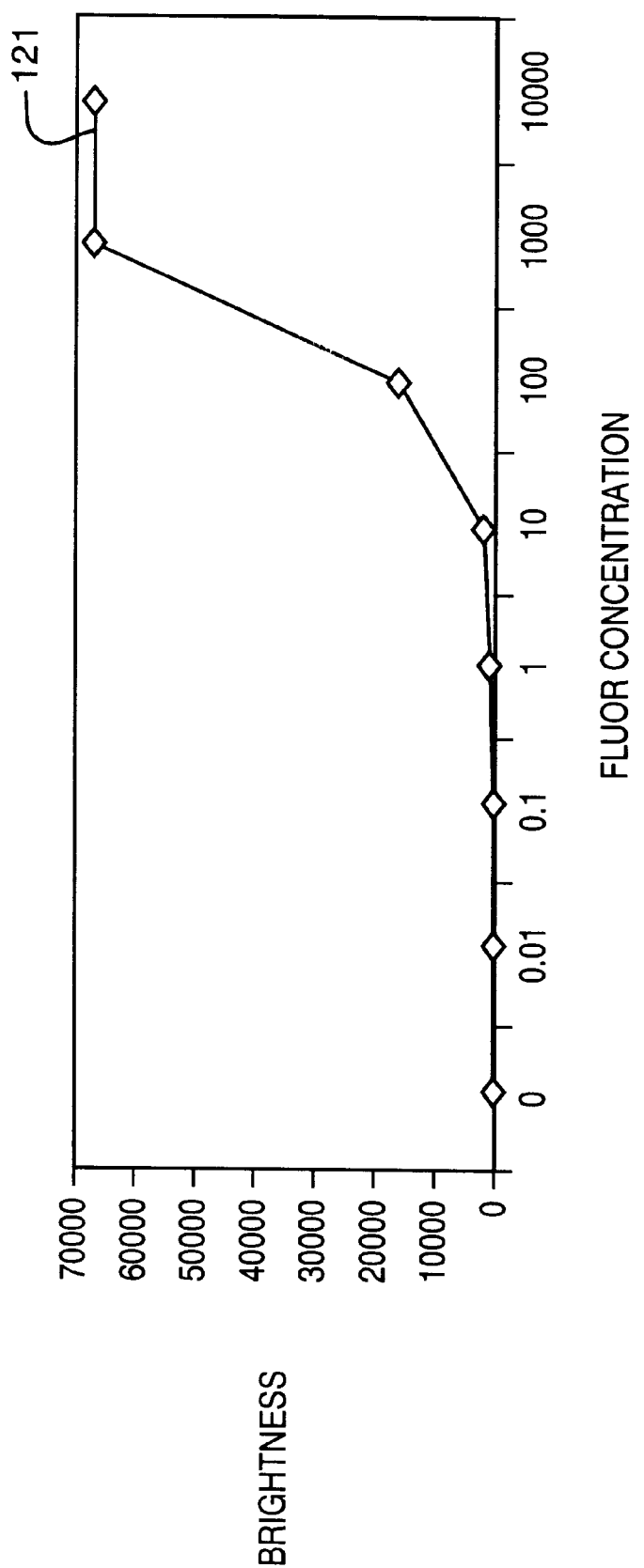
FIG. 3 is a diagram illustrating a fluorophore brightness as a function of fluorophore concentration.

It is known in the relevant art that the brightness characteristics of the hybridized spots 114 are typically nonlinear functions of the fluorophore concentration, as shown in FIG. 3. As exemplified by a concentration-to-brightness curve 121, a fluorophore may have a more useful response within a relatively narrow concentration range (e.g., from about $$10 \text{ to } 1000 \; \frac{\text{fluor}}{\mu m^2}$$

in the example provided), and an essentially flat response outside this concentration range. It is important to be able to measure the concentration-to-brightness curve on a known fluorescent sample for the purpose of quantifying the fluorophore concentration in the corresponding hybridized spot 114. Once the characteristic curve of the corresponding fluorescent imager has been determined, operational parameters of the microarray scanning system 10 can be specified.

Figure 4:
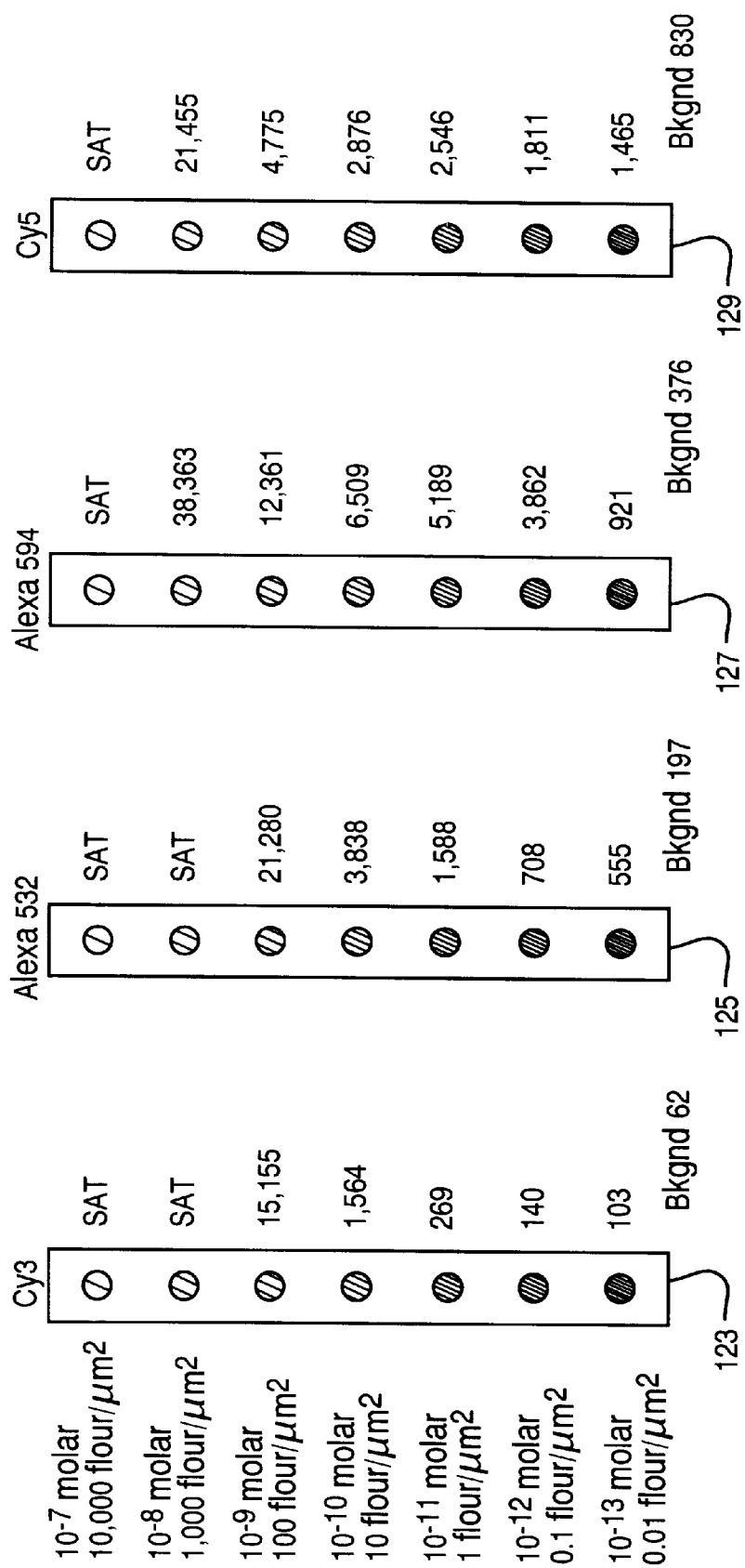
FIG. 4 is a diagram illustrating response of fluorophores at various concentrations to a constant level of incident excitation radiation.

By way of example, a comparison of various fluorescent dyes is provided in FIG. 4. In a Cy3 dilution fiducial series 123 containing seven individual dilution spots having fluorophore concentrations ranging from $$0.01 \; \frac{\text{fluor}}{\mu m^2} \text{ to } 10,000 \; \frac{\text{fluor}}{\mu m^2},$$

a brightness of 15,155 was measured at a concentration of $$100 \; \frac{\text{fluor}}{\mu m^2}$$

and saturation occurred at a concentration of $$1000 \; \frac{\text{fluor}}{\mu m^2}$$

for a constant level of incident excitation radiation. The signal values are average pixel values obtained in a 2 millimeter circle. For an Alexa532 dilution fiducial series 125, a concentration of $$100 \; \frac{\text{fluor}}{\mu m^2}$$

produced a measured brightness of 21,280. For an Alexa594 dilution fiducial series 127 and a concentration of $$1000 \; \frac{\text{fluor}}{\mu m^2},$$

the brightness measurement was 38,363, and for a Cy5 dilution fiducial series 129, saturation was reached at a concentration of $$10,000 \; \frac{\text{fluor}}{\mu m^2}.$$

If the sensitivity of the detector system 40 is set too high, saturated signals are produced, reducing the usefulness of the resulting data set. If, on the other hand, the sensitivity of the detector system 40 is set too low, the full resolution of the microarray scanning system 10 is not used and maximum differentiation in fluorescence levels between the hybridized spots 114 is not obtained. Moreover, if two or more channels of the microarray scanning system 10 are being used, the channels need to be balanced such that the dynamic range of the fluorophore sensitivity of each channel lies within the dynamic range of the microarray scanning system 10.

The computational device 60, in FIG. 1, includes dilution software 63, or other machine-readable code, for obtaining a concentration-to-brightness curve from the dilution spots 119. In a preferred embodiment, the dilution spots 119 are set by protocol, and the position and characteristics of the dilution spots 119 are predetermined. Prior to imaging the hybridized spots 114, the microarray scanning system 10 images the dilution spots 119 while adjusting any combination of: i) the emitted power of the excitation radiation source 21, ii) a high-voltage reference 43 in the photomultiplier tube 41, and iii) the gain of the variable-gain amplifier 45, for all applicable channels. The outputs of the excitation radiation source 21 and the photomultiplier tube 41 can typically be adjusted over a range of at least 100:1. This allows the sensitivity of the microarray scanning system 10 to be adjusted over a range of 10,000:1 or greater. The sensitivity of the microarray scanning system 10 can thus be optimized without the risk of photobleaching any of the hybridized spots 114 and 118 in the microarrays 111 and 115.

While the invention has been described with reference to particular embodiments, it will be understood that the present invention is by no means limited to the particular constructions and methods herein disclosed and/or shown in the drawings, but also comprises any modifications or equivalents within the scope of the claims.

What is claimed is:

1. A microarray scanning system consisting of:

a planar substrate supporting a plurality of target spots containing genetic material and a plurality of dilution spots, each dilution spot having a predetermined concentration of fluorophore material;

and a means for calibrating said microarray scanning system, wherein said means for calibrating consists of:

irradiating means for irradiating the substrate, means for adjusting the irradiating means to irradiate only the plurality of dilution spots without irradiating the target spots during a calibration operation;

means for detecting emission radiation produced by the dilution spot fluorophore material in response to the irradiating means irradiating only the dilution spots during a calibration operation;

means for deriving a plurality of brightness readings, each said brightness reading corresponding to the level of emission radiation detected at a corresponding dilution spot;

means for analyzing said plurality of brightness readings to obtain a fluorophore brightness characteristic associated with the substrate as a function of fluorophore concentration based on the predetermined concentrations of fluorophore in the dilution spots; and means for adjusting the sensitivity of said microarray scanning system for use of the system to scan the target spots on the substrate in a measurement operation, said means adjusting settings of one or more of the irradiating means and the means for detecting in response to said fluorophore brightness characteristic.

2. The microarray scanning system of claim 1 wherein said irradiating means comprises at least one member of the group consisting of a single-wavelength coherent optical source, a multiple-wavelength coherent optical source, and a broadband radiation source.

3. The micro-array scanning system of claim 2 wherein said irradiating means includes multiple sources operating in multiple channels, and said means for adjusting adjusts the sensitivity of the system to obtain readings over all of the channels that are within the dynamic range of the system.

4. The microarray scanning system of claim 1 wherein said means for detecting comprises an optical system.

5. The microarray scanning system of claim 4 wherein said optical system comprises a confocal system.

6. The microarray scanning system of claim 1 wherein said means for detecting comprises at least one member of the group consisting of a photomultiplier tube, an avalanche photodiode, and a solid state optical detection device.

7. The microarray scanning system of claim 1 wherein said means for deriving comprises a machine-readable code that is resident within the system.

8. The microarray scanning system of claim 1 wherein said means for adjusting the sensitivity comprises means for adjusting an output level of said irradiating means.

9. The microarray scanning system of claim 1 wherein said means for adjusting the sensitivity comprises means for adjusting an output signal of said means for detecting.

10. The microarray scanning system of claim 1 wherein said means for adjusting the sensitivity comprises means for adjusting a reference source in electrical communication with said means for detecting.

11. The microarray scanning system of claim 1 further comprising means for securing the substrate.

12. The microarray scanning system of claim 1 further comprising means for translating the substrate in at least two axes.

13. The micro-array scanning system of claim 1 wherein said means for adjusting adjusts i. an output level of said irradiating means, ii. an output signal of said means for detecting, iii. a reference source in electrical communication with said means for detecting, or iv. any combination of i–iii.

* * * * *